United States Patent [19]

Schön et al.

[11] Patent Number: 4,983,611

[45] Date of Patent: Jan. 8, 1991

[54] 3-SULFONYL-3,7-DIAZABICYCLO[3,3,1]NONANE INTERMEDIATES AND PHARMACEUTICAL METHOD

[75] Inventors: Uwe Schön, Burgdorf; Wolfgang Kehrbach, Hannover; Klaus-Ullrich Wolf, Uetze-Hänigsen, all of Fed. Rep. of Germany

[73] Assignee: Kali-Chemie Pharma GmbH, Hannover, Fed. Rep. of Germany

[21] Appl. No.: 401,749

[22] Filed: Sep. 25, 1989

Related U.S. Application Data

[62] Division of Ser. No. 214,032, Jun. 30, 1988, Pat. No. 4,906,640.

[30] Foreign Application Priority Data

Jul. 4, 1987 [DE] Fed. Rep. of Germany ....... 3722134

[51] Int. Cl.$^5$ .................... A61K 31/44; C07D 471/08
[52] U.S. Cl. ...................................... 514/300; 546/122
[58] Field of Search ........................ 546/122; 514/300

[56] References Cited

PUBLICATIONS

Hoerlein, Eur. J. Med. Chem.-Chimica Therapeutica, vol. 12(4), pp. 301-305 (1977).

Primary Examiner—Mary C. Lee
Assistant Examiner—Bernard J. Dentz
Attorney, Agent, or Firm—Foley & Lardner, Schwartz, Jeffery, Schwaab, Mack, Blumenthal & Evans

[57] ABSTRACT 3-sulfonyl-3,7-diazabicyclo[3,3,1]nonane compounds corresponding to the formula:

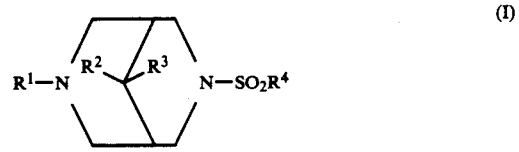

(I)

wherein
$R^1$ is alkyl, cycloalkylalkyl or benzyl,
$R^2$ is hydrogen or lower alkyl,
$R^3$ is hydrogen or lower alkyl or
$R^2$ and $R^3$ together form an alkylene chain, and
$R^4$ represents lower alkyl, thienyl, halogen substituted thienyl or a —$(CH_2)_n$—$R^5$ group, wherein n=0–3 and
$R^5$ is an optionally substituted phenyl group.

The compounds are pharmacologically active, particularly in influencing the motility of the stomach.

5 Claims, No Drawings

3-SULFONYL-3,7-DIAZABICYCLO[3,3,1]NONANE INTERMEDIATES AND PHARMACEUTICAL METHOD

This application is a division, of application Ser. No. 07/214,032, filed June 30, 1988, now U.S. Pat. No. 4,906,640.

BACKGROUND OF THE INVENTION

The present invention relates to new 3-sulfonyl-3,7-diazabicyclo[3,3,1]nonane compounds and their salts and pharmaceutical preparations containing such compounds and methods for producing such compounds.

3-alkanoyl- and 3-aroyl-3,7-diazabicyclo[3,3,1]nonane derivatives are known from DE-OS 26 58 558, for which central analgesic effects are cited. From U.S. Pat. No. 3,962,449 3,7-diazabicyclo[3,3,1]nonane derivatives substituted in the 3 and 7 positions by alkyl or phenylalkyl radicals and with anti-arrhythmic properties are known. 7-benzyl-3-phenylalkyl-3,7-diazabicyclo[3,3,1]nonane derivatives, likewise with anti-arrhythmic effects, are described in U.S. Pat. No. 4,183,935. Additional 3,7-diazabicyclo[3,3,1]nonane derivatives with properties affecting the heart, particularly anti-arrhythmic properties, are known from U.S. Pat. No. 4,550,112.

SUMMARY OF THE INVENTION

It is the object of the present invention to develop new 3,7-diazabicyclo[3,3,1]nonane compounds with valuable pharmacological properties.

It is also an object of the invention to provide a method for producing such new 3,7-diazabicyclo[3,3,1]nonane compounds and intermediate compounds useful in such method.

An additional object of the invention is to provide pharmaceutical compositions incorporating pharmaceutically effective amounts of such new 3,7-diazabicyclo[3,3,1]nonane compounds.

A further object of the invention is to provide a method for using such 3,7-diazabicyclo[3,3,1]nonane compounds, particularly in the treatment of stomach motility disturbances in mammals.

These and other objects of the invention are achieved by providing new 3-sulfonyl-3,7-diazabicyclo[3,3,1]nonane compounds corresponding to the Formula I,

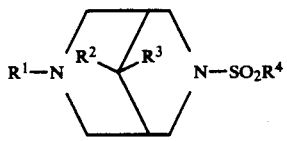
(I)

wherein
$R^1$ is an alkyl group with 1–6 carbon atoms, a cycloalkylalkyl group with 4–7 carbon atoms or benzyl,
$R^2$ is hydrogen or lower alkyl and
$R^3$ is hydrogen or lower alkyl or
$R^2$ and $R^3$ together form an alkylene chain with 3–6 carbon atoms, and
$R^4$ represents lower alkyl, thienyl, halogen substituted thienyl, or a $-(CH_2)_n-R^5$ group, wherein n=0–3 and
$R^5$ is a phenyl group or a phenyl group substituted by lower alkyl, lower alkoxy, halogen, trifluoromethyl or nitro, and pharmaceutically acceptable acid addition salts thereof.

According to a further aspect of the invention, the objects are achieved by providing a process for producing a 3-sulfonyl-3,7-diazabicyclo[3,3,1]nonane compound corresponding to the Formula I,

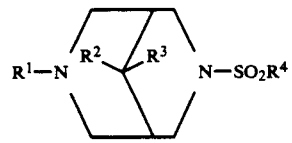
(I)

wherein
$R^1$ is an alkyl group with 1–6 carbon atoms, a cycloalkylalkyl group with 4–7 carbon atoms or a benzyl group,
$R^2$ is hydrogen or lower alkyl and
$R^3$ is hydrogen or lower alkyl or
$R^2$ and $R^3$ together form an alkylene chain with 3–6 carbon atoms, and
$R^4$ represents lower alkyl, thienyl, halogen substituted thienyl, or a $-(CH_2)_n-R^5$ group, wherein n=0–3, and
$R^5$ is a phenyl group or a phenyl group substituted by lower alkyl, lower alkoxy, halogen, trifluoromethyl or nitro,
or an acid addition salt thereof, said method comprising reacting a compound corresponding to the Formula II,

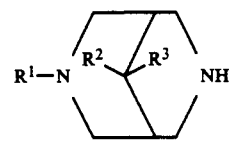
(II)

wherein $R^1$, $R^2$ and $R^3$ have the above meanings, with a sulfonic acid derivative corresponding to the Formula III,

$R^4\text{-}SO_2\text{-}X$ (III)

wherein $R^4$ has the above meaning and X represents a reactive group and optionally converting a free compound of Formula I into a corresponding acid addition salt or converting an acid addition salts of a compound of Formula I into the corresponding free base.

In yet another aspect of the invention the objects are achieved by providing a 2,4,6,8-tetraoxo-3,7-diazabicyclo[3,3,1]nonane compound corresponding to the Formula X,

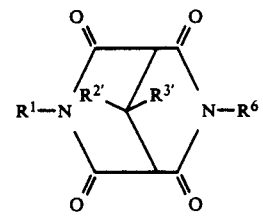
(X)

wherein $R^1$ is an alkyl group with 1-6 carbon atoms, a cycloalkylalkyl group with 4-7 carbon atoms or a benzyl group,
$R^{2'}$ is lower alkyl and
$R^{3'}$ is lower alkyl or
$R^{2'}$ and $R^{3'}$ together form an alkylene chain with 3-6 carbon atoms, and
$R^6$ is benzyl.

Objects of the invention are also achieved by providing a pharmaceutical composition comprising an effective stomach motility affecting amount of a 3-sulfonyl-3 7-diazabicyclo[3,3,1]nonane compound corresponding to the Formula I,

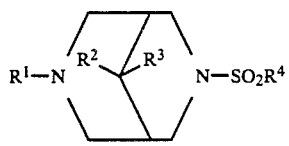
(I)

wherein
$R^1$ is an alkyl group with 1-6 carbon atoms, a cycloalkylalkyl group with 4-7 carbon atoms or benzyl,
$R^2$ is hydrogen or lower alkyl and
$R^3$ is hydrogen or lower alkyl or
$R^2$ and $R^3$ together form an alkylene chain with 3-6 carbon atoms, and
$R^4$ represents lower alkyl, thienyl, halogen substituted thienyl, or a —$(CH_2)_n$-$R^5$ group, wherein n=0-3 and
$R^5$ is a phenyl group or a phenyl group substituted by lower alkyl, lower alkoxy, halogen, trifluoromethyl or nitro,
or a pharmaceutically acceptable acid addition salt thereof and at least one pharmaceutical carrier or adjuvant.

Additional objects of the invention are achieved by providing a method of treating a stomach motility disturbance in a mammal comprising the step of ingesting into the stomach of said mammal an effective stomach motility improving amount of a 3-sulfonyl-3,7-diazabicyclo[3,3,1]nonane compound corresponding to the Formula I,

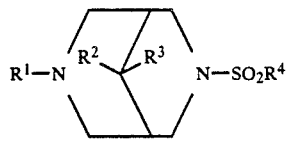
(I)

wherein
$R^1$ is an alkyl group with 1-6 carbon atoms, a cycloalkylalkyl group with 4-7 carbon atoms or benzyl,
$R^2$ is hydrogen or lower alkyl and
$R^3$ is hydrogen or lower alkyl or
$R^2$ and $R^3$ together form an alkylene chain with 3-6 carbon atoms, and
$R^4$ represents lower alkyl, thienyl, halogen substituted thienyl, or a —$(CH_2)_n$-$R^5$ group, wherein n=0-3 and
$R^5$ is a phenyl group or a phenyl group substituted by lower alkyl, lower alkoxy, halogen, trifluoromethyl or nitro,
or a pharmaceutically acceptable acid addition salt thereof.

DETAILED DESCRIPTION OF PREFERRED EMBODIMENTS

It has now been found that the new 3,7-diazabicyclo[3,3,1]-nonane compounds substituted in the 3 position by a sulfonyl radical possess valuable pharmacological properties and produce a beneficial pharmacological effect in the gastrointestinal tract. They are characterized in particular by a regulating effect on the motility of the stomach.

The present invention therefore relates to new 3-sulfonyl-3,7-diazabicyclo[3,3,1]nonane compounds of the general Formula I,

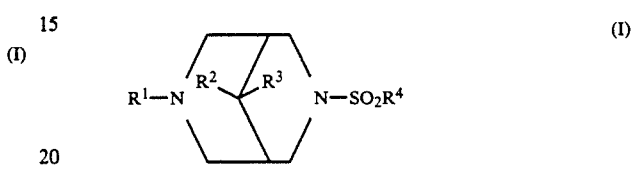
(I)

wherein
$R^1$ is an alkyl group with 1-6 carbon atoms, a cycloalkylalkyl group with 4-7 carbon atoms or benzyl,
$R^2$ is hydrogen or lower alkyl and
$R^3$ is hydrogen or lower alkyl or
$R^2$ and $R^3$ together form an alkylene chain with 3-6 carbon atoms, and
$R^4$ represents lower alkyl, for thienyl, which is optionally substituted by halogen, or for a —$(CH_2)_n$-$R^5$ group, wherein n=0-3 and
$R^5$ is a phenyl group, which is optionally substituted by lower alkyl, lower alkoxy, halogen, trifluoromethyl or nitro,
and their acid addition salts.

If in the compounds of Formula I $R^1$ represents an alkyl group, the latter may be straight-chain or branched and contain 1 to 6, preferably 2 to 5 carbon atoms. A cycloalkylalkyl group $R^1$ may contain 4 to 7 carbon atoms. Straight-chain alkyl radicals, e.g. the n-butyl radical, have been found to be particularly suitable $R^1$ radicals If the substituents $R^2$ and $R^3$ represent lower alkyl, these alkyl groups may be straight-chain or branched and contain 1 to 4, preferably 1 to 3 carbon atoms and represent methyl in particular. The alkyl groups $R^2$ and $R^3$ are advantageously of the same type, but may also be different. If $R^2$ and $R^3$ together form an alkylene chain, this may contain 3 to 6, preferably 4 to 5 carbon atoms.

If $R^4$ represents a lower alkyl group, this may be straight-chain or branched and contain 1 to 4 carbon atoms.

If $R^4$ represents thienyl, this may be unsubstituted or mono- or di-substituted by halogen. Chlorine or bromine are especially suitable as halogen substituents.

Preferably $R^4$ represents a —$(CH_2)_n$-$R^5$ group, wherein n represents 0 to 3, preferably 0. The phenyl group $R^5$ may be unsubstituted or mono-, di- or tri-substituted. The above named substituents are considered as substituents. Lower alkyl or alkoxy groups may be straight-chain or branched and contain 1 to 4 carbon atoms. Fluorine, chlorine, bromine or iodine are considered as halogen substituents. In multiple substitution the substituents preferably represent halogen, particularly chlorine, bromine or fluorine, lower alkyl, methoxy or nitro.

According to the invention, the new 3-sulfonyl-3,7-diazabicyclo[3,3,1]nonane compounds of the general Formula I and their acid addition salts are obtained by reacting in a known manner compounds of the general Formula II,

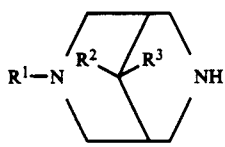

(II)

wherein $R^1$, $R^2$ and $R^3$ have the above meanings, with sulfonic acid derivatives of the general Formula III

(III)

wherein $R^4$ has the above meaning and X is a reactive group, and if desired converting free compounds of Formula I into their acid addition salts or converting the acid addition salts into the free compounds of Formula I.

The reaction of the sulfonic acid derivatives of Formula III with the 3,7-diazabicyclo[3,3,1]nonane compounds of Formula II may be carried out according to standard methods for formation of sulfonamides by acylation. Particularly sulfonic acid halides, preferably chlorides, and anhydrides of the sulfonic acids $R^4$-$SO_2$—OH are considered as reactive derivatives, e.g. compounds of Formula III, wherein the reactive group X is halogen, especially chlorine, or an O—$SO_2R^4$ group, wherein $R^4$ has the above meaning. The acylation may take place in a solvent which is inert under the reaction conditions at temperatures between 0° C. and the boiling temperature of the solvent. Halogenated hydrocarbons such as methylene chloride or chloroform, aromatic hydrocarbons such as benzene, toluene, xylene or chlorobenzene, cyclic ethers such as tetrahydrofuran or dioxane, dimethyl formamide or mixtures of these solvents are suitable as solvents. The acylation may be carried out if desired in the presence of a neutralizing agent. Inorganic bases, especially alkaline earth metal carbonates, or organic bases, especially tert. lower alkylamines and pyridines, such as triethylamine or 4-dimethylaminopyridine are suitable as neutralizing agents.

The compounds of Formula I may be isolated from the reaction mixture and purified in a known way. Acid addition salts may be converted into the free bases in the usual way and the latter converted in a known way into pharmacologically acceptable acid addition salts if desired. For example, suitable pharmacologically acceptable acid addition salts of compounds of Formula I include salts of such compounds with inorganic acids, e.g. halogen hydracids, especially hydrochloric acid, sulfuric acid or phosphoric acids, or with organic acids, for example lower aliphatic monocarboxylic or dicarboxylic acids such as lactic acid, maleic acid, fumaric acid or acetic acid, or sulfonic acids, for example lower alkyl sulfonic acids such as methane sulfonic acid or benzene-sulfonic acids optionally substituted in the benzene ring by halogen or lower alkyl such as p-toluene sulfonic acid or cyclohexylaminosulfonic acid.

If $R^2$ and $R^3$ are different, the compounds may exist in two stereoisomeric forms. The present invention comprises both the isomer mixtures and the pure isomers of these compounds of Formula I. Isomer mixtures may be separated into the individual isomers in a known way at the stage of the final compounds or at an intermediate product stage, for example by fractional crystallization or by separation using column chromatography.

The 3,7-diazabicyclo[3,3,1]nonane compounds of Formula II used as starting compounds are known from U.S. Pat. Nos. 4,183,935 and 4,550,112 and 3,962,449 and DE-OS 26 58 558, and/or may be produced in a known manner according to the methods described in these documents or analogously to the methods described in these documents.

For example, compounds of Formula II may be obtained by cleaving the benzyl group $R^6$ from compounds of Formula IV using hydrogenolysis in a known way.

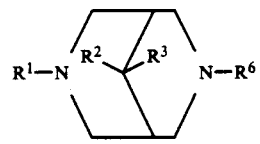

(IV)

wherein $R^1$, $R^2$ and $R^3$ have the above meanings and $R^6$ is benzyl. The hydrogenolytic cleavage of the $R^6$ group may take place with hydrogen in the presence of a palladium/carbon catalyst in an organic, protic, polar solvent, for example a lower alcohol such as ethanol. Hydrogenation may advantageously be carried out at room temperature and a hydrogen pressure of approximately 5 to 6 atmospheres.

Starting compounds of Formula IVa,

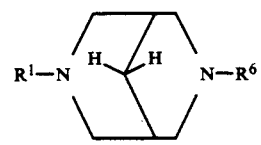

(IVa)

wherein $R^1$ and $R^6$ have the above meanings, may be obtained in a known way by reacting piperidone compounds of the general Formula V,

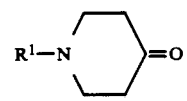

(V)

wherein $R^1$ has the above meaning, with amine compounds of the general Formula VI,

(VI)

wherein $R^6$ has the above meaning, and two moles of formaldehyde in a Mannich reaction to keto compounds of the general Formula VII,

(VII)

wherein $R^1$ and $R^6$ have the above meanings, and then reducing them. The reaction of the amines of Formula VI with formaldehyde and the piperidones of Formula V may take place under conditions usual for Mannich condensations. For instance, the reaction of the amine with the piperidone and formaldehyde, if desired in the form of paraformaldehyde, may take place in an organic solvent, for example a cyclic ether, a halogenated hydrocarbon or preferably a lower alcohol, in the presence of a quantity of an acid neutralizing the amine, for instance glacial acetic acid or hydrochloric acid. Advantageously, the reaction is carried out at room temperature. The reduction of the resulting keto compounds of Formula VII may be carried out according to usual methods for the reduction of ketones. The Wolff-Kishner reduction by means of hydrazine is especially suitable. For instance, the reaction with hydrazine may take place in the presence of an alkaline earth metal hydroxide in a solvent with a high boiling point, for instance triethylene glycol, at the boiling temperature of the solvent.

Compounds of Formula IVb,

(IVb)

wherein $R^1$ and $R^6$ have the above meanings and $R^7$ is lower alkyl, may be produced from the compounds of Formula VII by converting them in a known way first with an alkyl halide into the corresponding carbinols in a Grignard reaction and then converting the alcoholic hydroxy group into an easily cleavable group, e.g. a sulfonyloxy group, for instance the tosyloxy group, in a known way and cleaving the latter by reduction in a known way.

Compounds of Formula IVc,

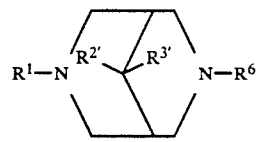

(IVc)

wherein $R^{2'}$ and $R^{3'}$ have the meanings given for $R^2$ and $R^3$ with the exception of hydrogen, and $R^1$ and $R^6$ have the above meaning, may be obtained, for example, starting with compounds of Formula VIII,

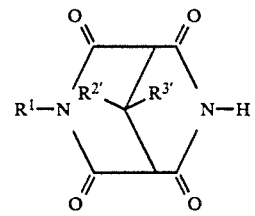

(VIII)

wherein $R^1$, $R^{2'}$ and $R^{3'}$ have the above meanings. For this, the tetraoxo compounds of Formula VIII are first reacted with benzyl halides of Formula IX, $R^6$-Hal (IX)

wherein $R^6$ has the above meaning and Hal stands for halogen, particularly chlorine or bromine, to the N,N'-di-substituted tetraoxo compounds of Formula X,

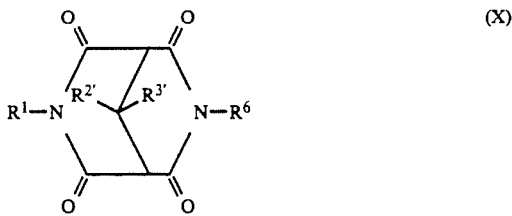

(X)

wherein $R^1$, $R^{2'}$, $R^{3'}$ and $R^6$ have the above meanings, and then these are reduced to the compounds of Formula IVc. The reaction of the diimide compounds of Formula VIII with the compounds of Formula IX may take place according to usual methods for the alkylation of imides.

The reaction advantageously takes place in a solvent which is inert under the reaction conditions in the presence of a base at high temperature, for instance the boiling temperature of the solvent. Thus for example alkaline earth metal carbonates or hydrides in dimethyl formamide or alkaline earth metal alcoholates in a lower alcohol are suitable. Benzyl halide is advantageously used in excess.

The 2,4,6,8-tetraoxo-3,7-diazabicyclo[3,3,1]nonane compounds of Formula VIII are known and/or can be produced according to the method described by Hoerlein (Eur. J. Med. Chem. 12, 301–305) by ring closure of 2,6-dioxo-3,5-dicyanopiperidine compounds of Formula XI,

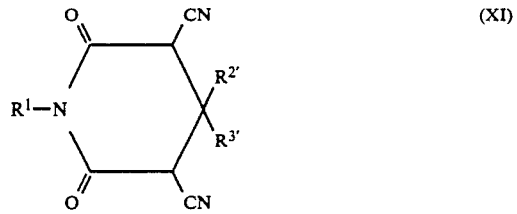

(XI)

wherein $R^1$, $R^{2'}$ and $R^{3'}$ have the above meanings, in high-percentage acid/water mixtures. The 2,6-dioxo-3,5-cyanopiperidines XI are themselves obtained in a known way by condensation of appropriately substituted alkylidene cyanoacetic esters of Formula XII,

(XII)

wherein $R^{2'}$ and $R^{3'}$ have the above meanings, with cyanoacetic amides of Formula XIII, $R^1$-NH—CO—CH$_2$—CN (XIII)

wherein $R^1$ has the above meaning.

The compounds of Formula I and their pharmacologically acceptable acid addition salts possess interesting pharmacological properties and are characterized in particular by a beneficial effect on the motility of the stomach. Thus in experiments on animals under the influence of compounds of Formula I, the peristaltic waves of the stomach were amplified without the frequency of the movements changing significantly.

Description of the pharmacological test methods:
I. Determination of the minimum toxic dose.

Male mice of 20–25 g weight were administered i.p. maximum doses of 200 mg/kg of the test substance. The animals were carefully observed for 3 hours for toxicity symptoms. In addition over a period of 24 hours after application, all toxic symptoms and instances of death were recorded. Accompanying symptoms were likewise observed and recorded. If death or strong toxic symptoms were observed, additional mice were administered increasingly smaller doses until no more toxic symptoms occurred. The lowest dose which caused death or strong toxic symptoms is given as the minimum toxic dose.

2 Determination of the effect on the motility of the stomach in anaesthetized rats.

Rats of the SIV 50 strain with a body weight of 180–250 g were anaesthetized with a ketamine/xylazine mixture on an empty stomach. The animals were tracheotomized and laparotomized. After a pylorus ligature was applied, a stomach probe was introduced into the stomach and connected at the other end to a calibrated pressure sensor (Statham element P 23 ID) by a three-way tap. Then the stomachs of the animals were filled via the probe with 2–3 ml water. The pressure fluctuations in the stomach were recorded before and after application of the test substances with the aid of a Watanabe Multicorder (MC 641). The differences between the mean amplitudes before and after treatment were determined and the change in the mean amplitudes caused by the test substances were given relative to the values obtained before treatment.

In the foregoing test methods the compounds show an increase in amplitude after i.p. application of 100 μmol/kg for instance, by the factors given in Table P below. The example numbers given in Table P relate to the following production examples.

TABLE P

| Test substance Example No. | Effect of promoting stomach motility in the rat Factor of increase in amplitude at dose of 100 μmol/k i.p. | Minimum toxic dose mg/kg mouse i.p. |
| --- | --- | --- |
| 1 | >10 | 200 |
| 2 | >10 | >200 |
| 3 | 8.8 | 200 |
| 4 | >10 | 100 |
| 6 | 6.7 | 200 |
| 7 | 5.7 | >200 |
| 8 | >10 | 100 |
| 9 | >10 | 200 |
| 10 | >10 | 200 |
| 17 | 5.0 | >200 |
| 18 | 7.3 | 200 |
| 23 | >10 | 200 |
| 26 | >10 | 100 |
| 27 | >10 | 200 |
| 29 | 9.4 | >200 |
| 31 | 3.5 | 200 |
| 32 | 1.9 | 200 |
| 34 | 7.9 | 200 |
| 36 | 4.6 | 200 |
| 37 | 4.2 | >200 |
| 41 | 8.8 | 200 |
| 43 | >10 | — |
| 48 | 4.8 | >200 |
| 54 | 10 | >200 |
| 56 | >10 | 100 |
| 58 | 9.3 | 200 |
| 61 | 4.2 | >200 |
| 62 | 3.0 | >200 |
| 66 | 4.7 | >200 |

As can be seen from the above data, the compounds according to the invention cause a considerable increase in the mean amplitudes of the peristaltic pressure waves of the stomach.

Because of these effects, the compounds of Formula I and their physiologically acceptable acid addition salts are suitable in gastroenterology as drugs for larger mammals, particularly humans, for prophylaxis and treatment of motility disturbances in the gastrointestinal tract. Thus the substances are useful, for example, for treating various complaints caused by motility disturbances of the gastrointestinal tract such as nausea, feeling of fullness or pains in the epigastrium.

The doses to be used can be varied individually and naturally vary according to the type of condition to be treated, the identity of the substance used and the manner of administration. For instance, parenteral formulations will generally contain less active substance than oral preparations. In general, however, medicinal forms with an active substance content of 5–50 mg per individual dose are suitable for administration to larger mammals, particularly humans.

As medicaments, the compounds of Formula I and their physiologically acceptable acid addition salts may be contained with standard pharmaceutical adjuvants or auxiliaries in galenic preparations such as tablets, capsules, suppositories or solutions. These galenic preparations may be produced according to known methods using standard solid carrier substances such as lactose, starch or talcum, or liquid diluents such as water, fatty oils or liquid paraffins, and using standard pharmaceutical auxiliaries, for instance tablet disintegrating agents, solubilizers or preservatives.

The following examples explain the invention in greater detail, but in no way limit its scope.

EXAMPLE 1

7-(n-butyl)-3-[(3,4-dichlorophenyl)-sulfonyl]-9,9-dimethyl-3,7-diazabicyclo[3,3,1]nonane.

A solution of 2.8 g (=0.0114 mol) 3,4-dichlorobenzene sulfonic acid chloride in 20 ml dichloromethane was added dropwise with ice cooling to a solution of 2.4 g (=0.0114 mol) 7-(n-butyl)-9,9-dimethyl-3,7-diazabicyclo[3,3,1]nonane (=substance No. C1 in the following Table C) in 40 ml dichloromethane. Then the ice bath was removed and the reaction mixture stirred further for 3 hours at room temperature. The hydrochloride of the title compound thereby precipitated as a white precipitate. In order to complete crystallization, the reaction mixture was allowed to stand 12 more hours in a refrigerator. Then the crystals were separated by suction filtration and dried at 60° C. in a vacuum drier. 3.3 g 7-(n-butyl)-3-[(3,4-dichlorophenyl)sulfonyl]-9,9-dimethyl-3,7-diazabicyclo[3,3,1]nonane hydrochloride with a melting point of 170°–173° C. were obtained.

EXAMPLE 2

7-benzyl-3-[(thien-2-yl)-sulfonyl]-9,9-dimethyl-3,7-diazabicyclo[3,3,1]nonane.

(A) A solution of 2.87 g (=0.015 mol) thiophene-2-sulfonyl chloride in 20 ml dichloromethane was added dropwise with ice cooling to a solution of 3.5 g (=0.014 mol) 7-benzyl-9,9-dimethyl-3,7-diazabicyclo[3,3,1]nonane (=substance No. C8 in the following Table (C)) in 40 ml dichloromethane. Then the ice bath was removed and the reaction mixture stirred further for 3 hours at room temperature. The reaction mixture was then made alkaline by adding aqueous sodium hydroxide solution, the aqueous phase was separated and extracted twice with dichloromethane. The combined dichloromethane phases were dried over magnesium sulfate and the solvent was evaporated. 4.0 g of the title compound (base) were thereby obtained as an oil.

(B) 4.0 g of the oily base obtained above were dissolved in 40 ml ethyl acetate, and a solution of 1.54 g tartaric acid in 40 ml acetone was added to the solution with ice cooling. The hydrogen tartrate of the title compound thereby precipitated out in crystalline form. The crystals were separated by suction filtration and dried at 50° C. in a vacuum drier. 4.3 g 7-benzyl-3-[(thien-2-yl)-sulfonyl]-9,9-dimethyl-3,7-diazabicyclo[3,3,1-]nonane hydrogen tartrate with a melting point of 148°–153° C. were obtained.

The compounds of Formula I listed in the following Table 1 were also obtained by methods analagous to the methods described in the foregoing Examples 1 and 2, starting with appropriate starting compounds corresponding to Formula II.

TABLE 1

| Example No. | $R^1$ | $R^2$ | $R^3$ | $R^4$ | Observations Melting point in °C. |
|---|---|---|---|---|---|
| 3 | n-$C_4H_9$ | $CH_3$ | $CH_3$ | phen-$(CH_2)_2$— | 1.4 Tart: 78 |
| 4 | n-$C_4H_9$ | $CH_3$ | $CH_3$ | phen | B: ol, Tart: am |
| 5 | n-$C_4H_9$ | $CH_3$ | $CH_3$ | 4-$CH_3$-phen | B: 85 |
| 6 | n-$C_4H_9$ | $CH_3$ | $CH_3$ | 2,5-di-$CH_3$-phen | 1.5 Tart: 85 |
| 7 | n-$C_4H_9$ | $CH_3$ | $CH_3$ | 2,4,6-tri-isoprop-phen | B: ol, Tart: am |
| 8 | n-$C_4H_9$ | $CH_3$ | $CH_3$ | 4-(n-$C_4H_9$)-phen | B: ol, Tart: am |
| 9 | n-$C_4H_9$ | $CH_3$ | $CH_3$ | 4-$CH_3$O-phen | B: ol, Tart: am |
| 10 | n-$C_4H_9$ | $CH_3$ | $CH_3$ | 2,5-di-$CH_3$O-phen | B: 72–73 |
| 11 | n-$C_4H_9$ | $CH_3$ | $CH_3$ | 3,4-di-$CH_3$O-phen | B: 94 |
| 12 | n-$C_4H_9$ | $CH_3$ | $CH_3$ | 2-Cl-phen | B: ol, Tart: am |
| 13 | n-$C_4H_9$ | $CH_3$ | $CH_3$ | 4-Cl-phen | HCl: 132–137 |
| 14 | n-$C_4H_9$ | $CH_3$ | $CH_3$ | 3-Cl-phen | Tart: 102 |
| 15 | n-$C_4H_9$ | $CH_3$ | $CH_3$ | 2,5-di-Cl-phen | B: ol, Tart: am |
| 16 | n-$C_4H_9$ | $CH_3$ | $CH_3$ | $CH_3$ | B: ol |
| 17 | n-$C_4H_9$ | $CH_3$ | $CH_3$ | 3,5-di-Cl-phen | 0.8 HCl: 194 |
| 18 | $C_2H_5$ | $CH_3$ | $CH_3$ | 3-Cl-phen | 1.4 Tart: 100 |
| 19 | n-$C_5H_{11}$ | $CH_3$ | $CH_3$ | 3-Cl-phen | Tart: 159–160 |
| 20 | n-$C_4H_9$ | $CH_3$ | $CH_3$ | 4-F-phen | B: ol, Tart: am |
| 21 | n-$C_4H_9$ | $CH_3$ | $CH_3$ | 4-F-3-Cl-phen | HCl: 165 |
| 22 | n-$C_4H_9$ | $CH_3$ | $CH_3$ | 4-Br-phen | HCl: 177–178 |
| 23 | n-$C_5H_{11}$ | $CH_3$ | $CH_3$ | 4-Br-phen | HCl: 218–222 |
| 24 | n-$C_4H_9$ | $CH_3$ | $CH_3$ | 4-J-phen | HCl: 222–227 |
| 25 | n-$C_4H_9$ | $CH_3$ | $CH_3$ | 2-$CF_3$-phen | B: 63 |
| 26 | n-$C_4H_9$ | $CH_3$ | $CH_3$ | 3-$CF_3$-phen | HCl: 114 |
| 27 | n-$C_4H_9$ | $CH_3$ | $CH_3$ | 4-$NO_2$-phen | 1.55 HCl: 79 |
| 28 | n-$C_4H_9$ | $CH_3$ | $CH_3$ | 2-$NO_2$-phen | Tart: 173 |
| 29 | n-$C_4H_9$ | $CH_3$ | $CH_3$ | 3-$NO_2$-4-Cl-phen | B: 73–75 |
| 30 | n-$C_4H_9$ | n-$C_3H_7$ | n-$C_3H_7$ | 4-Br-phen | HCl: 157–158 |
| 31 | n-$C_4H_9$ | $CH_3$ | $CH_3$ | 2-$CH_3$-6-Cl-phen | B: ol, Tart: am |
| 32 | n-$C_4H_9$ | $CH_3$ | $CH_3$ | 2-$CH_3$O-5-Br-phen | B: 65–68 |
| 33 | n-$C_4H_9$ | $CH_3$ | $CH_3$ | 2-thien | HCl: 213 |
| 34 | $C_2H_5$ | $CH_3$ | $CH_3$ | 2-thien | B: 94–96 |
| 35 | n-$C_5H_{11}$ | $CH_3$ | $CH_3$ | 2-thien | B: ol, Tart: am |
| 36 | n-$C_4H_9$ | $CH_3$ | $CH_3$ | 5-Cl-2-thien | B: ol, Tart: am |
| 37 | n-$C_4H_9$ | $CH_3$ | $CH_3$ | 4,5-di-Br-2-thien | B: 68 |
| 38 | n-$C_4H_9$ | $CH_3$ | $CH_3$ | 2,5-di-Cl-3-thien | 1.25 Tart: 84–88 |
| 39 | $(CH_3)_2$CH— | $CH_3$ | $CH_3$ | 4-Br-phen | B: 140 |
| 40 | $(CH_3)_2$CH— | $CH_3$ | $CH_3$ | 3-Cl-phen | B: 130 |
| 41 | $(CH_3)_2$CH— | $CH_3$ | $CH_3$ | 2-thien | B: 98 |
| 42 | Cyclohex-$CH_2$— | $CH_3$ | $CH_3$ | 4-Br-phen | B: ol, Tart: am |
| 43 | Cyclohex-$CH_2$— | $CH_3$ | $CH_3$ | 3-Cl-phen | B: ol, Tart: am |
| 44 | Cyclohex-$CH_2$— | $CH_3$ | $CH_3$ | 2-thien | B: ol, Tart: am |
| 45 | $CH_3$ | H | H | 4-$CH_3$-phen | B: 97 |
| 46 | n-$C_4H_9$ | H | H | 4-$CH_3$-phen | B: 55 |
| 47 | n-$C_4H_9$ | H | H | 4-Br-phen | B: 165–166 |
| 48 | $CH_3$ | H | H | 4-Br-phen | B: 196 |
| 49 | n-$C_4H_9$ | H | H | 2-thien | 1.3 Tart: 113 |
| 50 | phen-$CH_2$— | H | H | 4-$CH_3$-phen | B: 132 |
| 51 | phen-$CH_2$— | H | H | 3-Cl-phen | B: 159 |
| 52 | phen-$CH_2$— | H | H | 2-thien | Tart: 100 |
| 53 | phen-$CH_2$— | $CH_3$ | $CH_3$ | 4-Br-phen | Tart: 149–150 |
| 54 | phen-$CH_2$— | $CH_3$ | $CH_3$ | 4-F-phen | Tart: 99–100 |
| 55 | phen-$CH_2$— | $CH_3$ | $CH_3$ | 3-Cl-phen | B: ol, Tart: am |
| 56 | n-$C_4H_9$ | $CH_3$ | $CH_3$ | phen-$CH_2$— | B: 113 |
| 57 | n-$C_4H_9$ | —$(CH_2)_5$— | | 4-Br-phen | HCl: 211 |
| 58 | n-$C_4H_9$ | —$(CH_2)_5$— | | 3-Cl-phen | Tart: 202 |
| 59 | n-$C_4H_9$ | —$(CH_2)_5$— | | 2-thien | B: 97 |
| 60 | $(CH_3)_2$CH—$CH_2$— | —$(CH_2)_5$— | | 4-Br-phen | B: 135 |
| 61 | $(CH_3)_2$CH—$CH_2$— | —$(CH_2)_5$— | | 3-Cl-phen | B: 134–135 |
| 62 | Cyclohex-$CH_2$— | —$(CH_2)_5$— | | 4-Br-phen | B: 143–145 |
| 63 | Cyclohex-$CH_2$— | —$(CH_2)_5$— | | 2-thien | B: 112 |
| 64 | n-$C_4H_9$ | n-$C_3H_7$ | n-$C_3H_7$ | 2-thien | B: 83 |
| 65 | n-$C_4H_9$ | n-$C_3H_7$ | n-$C_3H_7$ | 3,4-di-Cl-phen | B: 96 |

TABLE 1-continued

| Example No. | $R^1$ | $R^2$ | $R^3$ | $R^4$ | Observations Melting point in °C. |
|---|---|---|---|---|---|
| 66 | n-C$_4$H$_9$ | n-C$_3$H$_7$ | n-C$_3$H$_7$ | 3-Cl-phen | B: 45–48, HCl: 124–126 |

B = Base,
thien = Thienyl,
HCl = Hydrochloride,
phen = Phenyl,
cyclohex = Cyclohexyl
am = amorphous
isoprop = Isopropyl
Tart = Hydrogentartrate
ol = oily The starting materials used were produced in accordance with the following general operating directions:

(A) General operating directions for producing 3,7-di-substituted 2,4,6,8-tetraoxo-3,7-diazabicyclo[3,3,1]nonane compounds of Formula X by reacting 2,4,6,8-tetraoxo-3,7-diazabicyclo[3,3,1]nonane compounds of Formula VIII with benzyl halides of Formula IX.

(a) Reaction of N-mono-substituted compounds of Formula VIII, wherein $R^1$ is other than hydrogen:

A mixture of 0.1 mol of the imide compound of Formula VIII, 0.2 mol potassium carbonate and 0.15 mol benzyl halide of Formula IX in 390 ml dimethyl formamide was heated for 3 to 7 hours under reflux. The inorganic salt precipitate which formed was removed by filtering, and the clear solution was evaporated to dryness. The remaining residue was dissolved in water and ethyl acetate. The organic solution was separated, washed twice with water, dried over magnesium sulfate, filtered and evaporated. If the resulting tetraoxo compounds of Formula X then appear in crystalline form, simple recrystallization is sufficient for further purification. Otherwise, it may be necessary to purify the resulting crude product by column chromatography over silica gel or aluminum oxide using, for example, ethyl acetate/hexane mixtures as eluents.

(b) Reaction of compounds of Formula VIII, wherein $R^1$ is hydrogen:

For di-substitution of the compounds of Formula VIII in which $R^1$ is hydrogen, by the benzyl halides of Formula IX, the foregoing general operating directions for mono-substitution of the compounds of Formula VIII in which $R^1$ is other than hydrogen, were modified. Instead of the reaction mixture given above, a mixture of 0.1 mol of the tetraoxo compound of Formula VIII, 0.25 mol of potassium carbonate and 0.3 mol benzyl halide of Formula IX in 300 ml dimethyl formamide were used.

The compounds listed in the following Table A were produced according to the foregoing general operating directions.

TABLE A

Compounds of Formula X

| Compound | $R^1$ | $R^{2'}$ | $R^{3'}$ | $R^6$ | Remarks |
|---|---|---|---|---|---|
| A1 | n-C$_4$H$_9$ | CH$_3$ | CH$_3$ | benz | mp: 110 |
| A2 | C$_2$H$_5$ | CH$_3$ | CH$_3$ | benz | oil |
| A3 | n-C$_5$H$_{11}$ | CH$_3$ | CH$_3$ | benz | mp: 85–86 |
| A4 | n-C$_4$H$_9$ | —(CH$_2$)$_5$— | | benz | mp: 100 |
| A5 | n-C$_4$H$_9$ | n-C$_3$H$_7$ | n-C$_3$H$_7$ | benz | oil |
| A6 | (CH$_3$)$_2$CH— | CH$_3$ | CH$_3$ | benz | mp: 170–174 |
| A7 | cyclohex-me | CH$_3$ | CH$_3$ | benz | mp: 129–131 |
| A8 | benz | CH$_3$ | CH$_3$ | benz | mp: 155–157 |
| A9 | (CH$_3$)$_2$CH—CH$_2$— | —(CH$_2$)$_5$— | | benz | mp: 126–128 |
| A10 | cyclohex-me | —(CH$_2$)5— | | benz | mp: 137 | mp = melting point in °C.
benz = benzyl
cyclohex-me = cyclohexylmethyl
*oil = was processed further as an oil (B) General operating directions for the reduction of 2,4,6,8-tetraoxo-3,7-diazabicyclo[3,3,1]nonane compounds of Formula X to 3,7-diazabicyclo[3,3,1]nonane compounds of Formula IVc.

0.1 mol lithium aluminum hydride in 100 ml of a solution of 70 ml absolute tetrahydrofuran and 30 ml absolute toluene were heated in a three-necked flask in an oil bath to a temperature of 80° C. Then 0.025 mol of the tetraoxo compound in 100 ml of a 70/30 mixture of tetrahydrofuran/toluene were slowly added dropwise. The reaction mixture was allowed to react for 2 to 4 hours at 120° C. Then it was hydrolyzed and extracted with methylene chloride under basic conditions. The organic phase was separated, dried over magnesium sulfate and evaporated. The resulting 3,7-diazabicyclo[3,3,1]nonane compounds were separated by bulb tube distillation at reduced pressure.

The 3,7-diazabicyclo[3,3,1]nonane compounds of Formula IVc given in the following Table B were produced according to these general operating directions for reduction by means of lithium aluminum hydride.

TABLE B

Compounds of Formula IVc

| Compound | $R^1$ | $R^{2'}$ | $R^{3'}$ | $R^6$ | Remarks |
|---|---|---|---|---|---|
| B1 | n-C$_4$H$_9$ | CH$_3$ | CH$_3$ | benz | bp: 170 |
| B2 | C$_2$H$_5$ | CH$_3$ | CH$_3$ | benz | bp: 185–19 |
| B3 | n-C$_5$H$_{11}$ | CH$_3$ | CH$_3$ | benz | bp: 160–17 |
| B4 | n-C$_4$H$_9$ | —(CH$_2$)$_5$— | | benz | bp: 220 |

TABLE B-continued

Compounds of Formula IVc

| Compound | R¹ | R²' | R³' | R⁶ | Remarks |
|---|---|---|---|---|---|
| B5 | n-C$_4$H$_9$ | n-C$_3$H$_7$ | n-C$_3$H$_7$ | benz | bp: 200 |
| B6 | (CH$_3$)$_2$CH— | CH$_3$ | CH$_3$ | benz | bp: 150 |
| B7 | cyclohex-me | CH$_3$ | CH$_3$ | benz | bp: 170 |
| B8 | benz | CH$_3$ | CH$_3$ | benz | bp: 230 |
| B9 | (CH$_3$)$_2$CH—CH$_2$— | —(CH$_2$)$_5$— | | benz | bp: n.d. |
| B10 | cyclohex-me | —(CH$_2$)$_5$— | | benz | mp: 95 | benz = benzyl
cyclohex-me = cyclohexylmethyl
n.d. = not determined, processed further without purification
bp = boiling point in °C. (0.01 Torr)
mp = melting point in °C.

(C) General operating directions for de-benzylation of the 3,7-di-substituted 3,7-diazabicyclo[3,3,1]nonane compounds of Formula IV to N-mono-substituted 3,7-diazabicyclo[3,3,1]nonane compounds of Formula II.

0.2 mol of a compound of Formula IV were dissolved in 600 ethanol and 10 g palladium/carbon catalyst were added to the solution. The reaction mixture was hydrogenated at room temperature under a hydrogen pressure of 5 atmospheres for approximately 6 hours. After hydrogenation had ended, the solution was separated from the catalyst and evaporated. The resulting compounds of Formula II were isolated by bulb tube distillation at reduced pressure.

The 3,7-diazabicyclo[3,3,1]nonane compounds of Formula II listed in the following Table C were produced according to the foregoing general directions for de-benzylation.

TABLE C

Compounds of Formula II

| Compound | R¹ | R² | R³ | Remarks |
|---|---|---|---|---|
| C1 | n-C$_4$H$_9$ | CH$_3$ | CH$_3$ | bp: 145 |
| C2 | C$_2$H$_5$ | CH$_3$ | CH$_3$ | bp: 131 |
| C3 | n-C$_5$H$_{11}$ | CH$_3$ | CH$_3$ | bp: 150 |
| C4 | n-C$_4$H$_9$ | —(CH$_2$)$_5$— | | n.d. |
| C5 | n-C$_4$H$_9$ | n-C$_3$H$_7$ | n-C$_3$H$_7$ | bp: 220 (1.5 Torr) |
| C6 | (CH$_3$)$_2$CH— | CH$_3$ | CH$_3$ | bp: 150 |
| C7 | cyclohex-me | CH$_3$ | CH$_3$ | n.b. |
| C8 | benz | CH$_3$ | CH$_3$ | bp: 180 |
| C9 | (CH$_3$)$_2$CH—CH$_2$— | —(CH$_2$)$_5$— | | bp: 180 |
| C10 | cyclohex-me | —(CH$_2$)$_5$— | | bp: 220 | benz = benzyl
cyclohex-me = cyclohexylmethyl
n.d. = not determined, processed further without purification
bp = boiling point in °C. (0.01 Torr)

EXAMPLE I

Tables containing 7-(n-butyl)-3-[(3,4-dichlorophenyl)sulfonyl]-9,9-dimethyl-3,7-diazabicyclo[3,3,1]nonane hydrochloride.

Tablets with the following composition per tablet were produced:

| | |
|---|---|
| 7-(n-butyl)-3-[(3,4-dichlorophenyl)-sulfonyl]-9,9-dimethyl-3,7-diazabicyclo[3,3,1]nonane hydrochloride | 20 mg |
| Cornstarch | 60 mg |
| Lactose | 135 mg |
| Gelatine (as 10% solution) | 6 mg |

The active substance, the cornstarch and the lactose were mixed with the 10% gelatine solution. The paste was ground and the resulting granulate was placed on a suitable tray and dried. The dried granulate was passed through a pulverizer and mixed in a mixer with the following additional adjuvants:

| | |
|---|---|
| Talcum | 5 mg |
| Magnesium stearate | 5 mg |
| Cornstarch | 9 mg | and then pressed into 240 mg tablets.

The foregoing description and examples have been set forth merely to illustrate the invention and are not intended to be limiting. Since modifications of the illustrative embodiments incorporating the spirit and substance of the invention may occur to persons skilled in the art, the scope of the invention should be limited solely with respect to the appended claims and equivalents.

We claim:

1. A 2,4,6,8-tetraoxo-3,7-diazabicyclo[3,3,1]nonane compound corresponding to the formula X, $$R^1-N\underset{\underset{O}{\parallel}}{\overset{\overset{O}{\parallel}}{\diagup}}\underset{R^{2'}}{\diagdown}\underset{R^{3'}}{\diagup}\underset{\underset{O}{\parallel}}{\overset{\overset{O}{\parallel}}{\diagdown}}N-R^6 \quad (X)$$

wherein
R¹ is n-C$_4$H$_9$, C$_2$H$_5$, n-C$_5$H$_{11}$, (CH$_3$)$_2$CH—, (CH$_3$)$_2$CH—CH$_2$—, a cycloalkylalkyl group with 4–7 carbon atoms or a benzyl group,
R²' is lower alkyl and
R³' is lower alkyl or
R²' and R³' together form an alkylene chain with 3–6 carbon atoms, and
R⁶ is benzyl.

2. A method of treating a stomach motility disturbance in a mammal comprising the step of ingesting into the stomach of said mammal an effective stomach motility improving amount of a 3-sulfonyl-3,7-diazabicyclo[3,3,1]nonane compound corresponding to the Formula I, $$R^1-N\diagup\underset{R^2}{\diagdown}\underset{R^3}{\diagup}\diagdown N-SO_2R^4 \quad (I)$$

wherein
- $R^1$ is an alkyl group with 1–6 carbon atoms, a cycloalkylalkyl group with 4–7 carbon atoms or benzyl,
- $R^2$ is hydrogen or lower alkyl and
- $R^3$ is hydrogen or lower alkyl or
- $R^2$ and $R^3$ together form an alkylene chain with 3–6 carbon atoms, and
- $R^4$ represents lower alkyl, thienyl, halogen substituted thienyl, or a $-(CH_2)_n-R^5$ group, wherein n=0–3 and
- $R^5$ is a phenyl group or a phenyl group substituted by lower alkyl, lower alkoxy, halogen, trifluoromethyl or nitro, or a pharmaceutically acceptable acid addition salt thereof.

3. A method according to claim 2, wherein $R^4$ represents thienyl, halogen substituted thienyl, or a $-(CH_2)_2-R^5$ group.

4. A method according to claim 3, wherein $R^4$ represents a group $R^5$.

5. A method according to claim 2, wherein $R^2$ and $R^3$ are each methyl.

* * * * *